US00PP24603P2

(12) United States Plant Patent
Hansen

(10) Patent No.: US PP24,603 P2
(45) Date of Patent: Jul. 1, 2014

(54) ***SEDUM* PLANT NAMED 'CHERRY TART'**

(50) Latin Name: ***Sedum* hybrid**
Varietal Denomination: Cherry Tart

(71) Applicant: Christopher M. Hansen, Holland, MI (US)

(72) Inventor: Christopher M. Hansen, Holland, MI (US)

( * ) Notice: Subject to any disclaimer, the term of this patent is extended or adjusted under 35 U.S.C. 154(b) by 124 days.

(21) Appl. No.: 13/573,625

(22) Filed: Sep. 27, 2012

(51) Int. Cl.
*A01H 5/00* (2006.01)

(52) U.S. Cl.
USPC ..... Plt./479

(58) Field of Classification Search
USPC ..... Plt./479
See application file for complete search history.

*Primary Examiner* — Susan McCormick Ewoldt
(74) *Attorney, Agent, or Firm* — Penny J. Aguirre

(57) ABSTRACT

A new cultivar of *Sedum* plant named 'Cherry Tart' characterized by its foliage that is red in color with the red coloration retained without fading in spring, summer and fall, its leaves that are thick, ovate in shape, and with only slightly serrated, its production of 30 to 40 crowns the first year after vernalization, its numerous large inflorescences with flowers that are dark pink in color.

2 Drawing Sheets

Botanical classification: *Sedum* hybrid.
Variety denomination: 'Cherry Tart'.

CROSS REFERENCE TO A RELATED APPLICATION

This application is co-pending with a U.S. Plant Patent Application filed for a plant derived from the same breeding program that is entitled *Sedum* Plant Named 'Lime Zinger' (U.S. Plant patent application Ser. No. 13/573,635).

BACKGROUND OF THE INVENTION

The present invention relates to a new and distinct cultivar of *Sedum* plant, botanically of hybrid origin and known as *Sedum* 'Cherry Tart' and will be referred to hereinafter by its cultivar name, 'Cherry Tart'. The new cultivar of *Sedum* is a hardy herbaceous perennial grown for use as a landscape and container plant and for use as a groundcover.

'Cherry Tart' arose from an ongoing breeding program by the Inventor in Hudsonville, Mich. The objective was to obtain a new cultivar of *Sedum* with dark cherry red foliage there is retained throughout the growing season combined with a compact mounded habit without the tendency to flop open in the center of the plant.

The new cultivar arose from a controlled cross made in July of 2009 between unnamed plants from the Inventors breeding program as male and female parents. The Inventor selected 'Cherry Tart' as a single unique plant in September of 2010 from the resulting seedlings.

Asexual reproduction of the new cultivar was first accomplished by tip stem cuttings in July of 2010 in Hudsonville, Mich. Propagation has determined the characteristics to be stable and reproduced true to type in successive generations.

SUMMARY OF THE INVENTION

The following traits have been repeatedly observed and are determined to be the characteristics of the new cultivar. These attributes in combination distinguish 'Cherry Tart' as a unique cultivar of *Sedum*.

1. 'Cherry Tart' exhibits foliage that is deep red in color with the red coloration retained without fading in spring, summer and fall.
2. 'Cherry Tart' exhibits leaves that are thick, ovate in shape, with only slightly serrated margins (unique for a groundcover type *Sedum*).
3. 'Cherry Tart' exhibits 30 to 40 crowns the first year after vernalization (unique for a groundcover type *Sedum*).
4. 'Cherry Tart' exhibits numerous large (10 cm in diameter) inflorescences with flowers that are dark pink in color.

The female parent differs from 'Cherry Tart' in being much shorter in height (70% shorter), and in having much smaller inflorescences, blue-gray foliage and much smaller leaves. The male parent differs from 'Cherry Tart' in being much taller in height and in having an upright plant habit, blue-gray foliage, and leaves that are larger in size. 'Cherry Tart' can be most closely compared to *Sedum* 'Voodoo' (not patented), *Sedum* 'Fulda Glow' (not patented), and 'Lime Zinger'. 'Voodoo' is similar to 'Cherry Tart' in having a groundcover type plant habit and in having red foliage. 'Voodoo' differs from 'Cherry Tart' in having much smaller leaves that are more heavily serrated, smaller inflorescences that bloom earlier in the summer, thinner foliage and in showing more variability as it is a seed strain. 'Fulda Glow' is similar to 'Cherry Tart' in being a groundcover type plant and in having red colored leaves. 'Fulda Glow' differs from 'Cherry Tart' in having smaller leaves, foliage that turns green-red in the summer, smaller inflorescences that bloom 6 to 8 weeks earlier in the summer, thinner leaves and in showing more variability as it is grown as a seed strain. 'Lime Zinger' differs from 'Cherry Tart' most significantly in having lime green leaves with red picotee margins and in having more branched stems.

BRIEF DESCRIPTION OF THE DRAWINGS

The accompanying colored photographs illustrate the overall appearance and distinct characteristics of the new *Sedum*.

The photographs were taken of a 14 month-old plant of 'Cherry Tart' and comparison plants as grown in a trial garden in Hudsonville, Mich.

Figure 1:
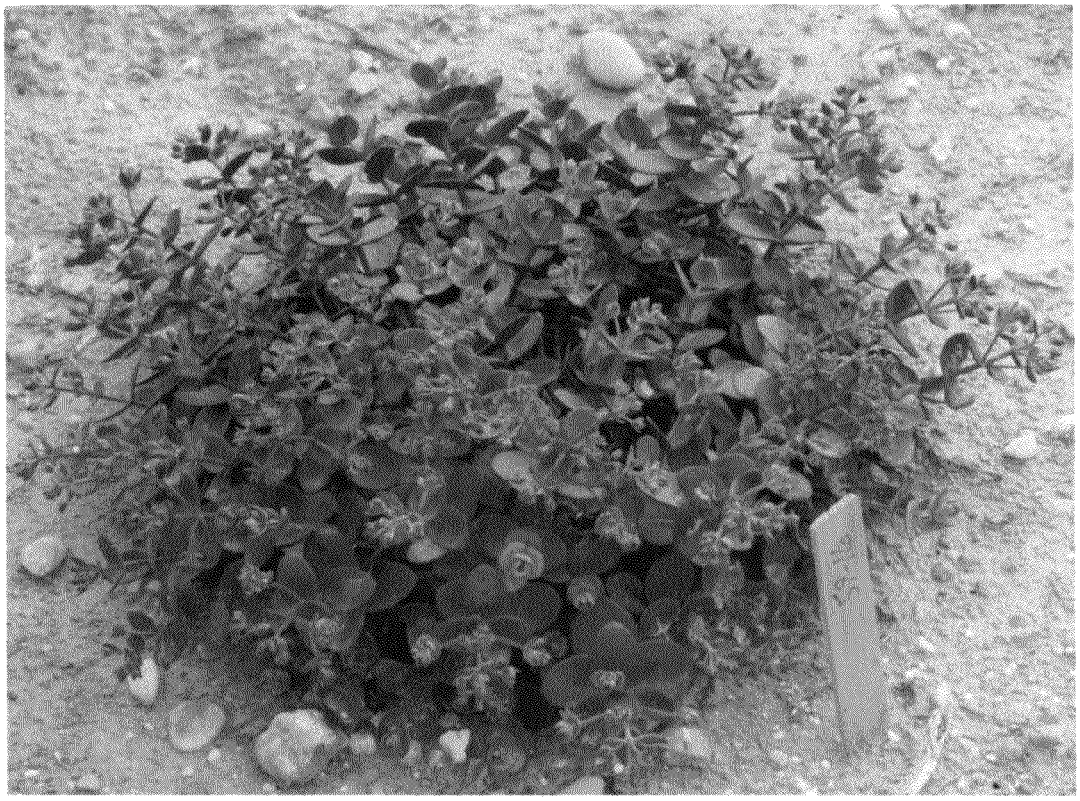

The photograph in FIG. 1 illustrates the plant habit of 'Cherry Tart'.

Figure 2:
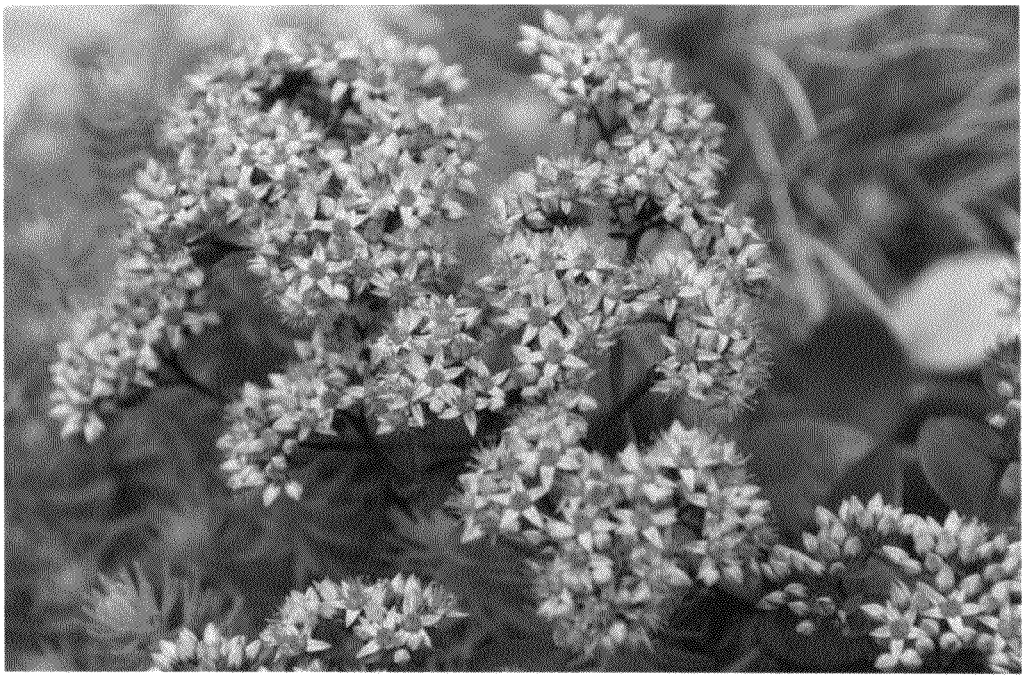

The photograph in FIG. 2 illustrates the inflorescences of 'Cherry Tart'.

Figure 3:
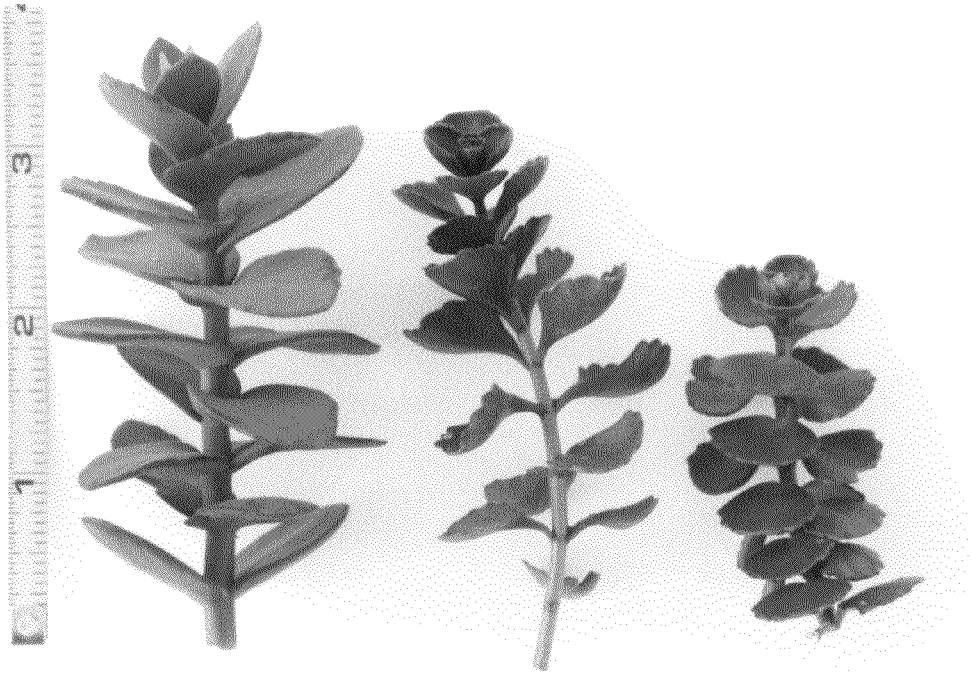

The photograph in FIG. 3 provides a comparison of the foliage of 'Cherry Tart' (left), 'Voodoo' (center), and 'Fulda Glow' (right). The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 14 month-old plants of 'Cherry Tart' as grown in a garden in Hudsonville, Mich. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General description:

*Blooming period.*—5 weeks in mid to late summer.

*Plant type*.—Herbaceous perennial.

*Plant habit*.—Compact, mound, groundcover of medium growing height for *Sedums*.

*Height and spread*.—Reaches about 15 cm in height and about 45 cm in spread.

*Hardiness*.—At least in U.S.D.A. Zones 4 to 9.

*Diseases pest*.—Highly resistant to *Sedum* foliage blight, no occurrence observed in a 3 year period.

*Root description*.—Fibrous.

*Propagation*.—Tip stem cuttings.

*Growth rate*.—Vigorous.

Stem description:

*Stem shape*.—Round.

*Stem size*.—Averages 16 cm in length (including terminal peduncle) and about 4 mm in width.

*Internode length*.—Average of 1.3 cm.

*Stem color*.—Spring growth; 145B and a blend of 145B and 183B towards base, mid summer; 183C.

*Stem surface*.—Glabrous.

*Branching habit*.—Basal or near-basal branching.

Foliage description:

*Leaf shape*.—Ovate.

*Leaf division*.—Simple.

*Leaf arrangement*.—Whorled (sometime opposite).

*Leaf base*.—Cordate around stem.

*Leaf apex*.—Broadly acute.

*Leaf venation*.—Not conspicuous, color matched leaf color.

*Leaf margins*.—Primarily entire with slight serrations.

*Leaf attachment*.—Sessile.

*Leaf presence and orientation*.—Nearly horizontal.

*Leaf texture*.—Thick, succulent.

*Leaf surface*.—Slightly glandular and slightly glaucous on upper and lower surface.

*Leaf color*.—Young growth; upper and lower surface 138B and becoming flushed with N77A as they mature in spring, mature foliage; spring, summer and fall upper and lower surface, N77A with slight tinge of N79C, non-fading.

*Leaf size*.—Up to 1.9 cm in length and 1.2 cm in width.

Flower description:

*Inflorescence type*.—Dense, slightly rounded cymes with an average of 6 terminal forked branches (each with 3 cymes) at terminus and upper lateral nodes.

*Inflorescence size*.—An average of 10 cm in diameter and 12 cm in depth (inclusive of all branches per stem).

*Lastingness of inflorescence*.—About 5 weeks.

*Flower type*.—Perfect, spreading, 5-starred.

*Flower number*.—An average of 90 flowers per branched cyme, about 500 flowers per stem.

*Flower fragrance*.—None.

*Flower buds*.—Conical in shape, about 4 mm length and 2.5 mm in diameter, ribbed surface, color; N74C with shadings and stripes of 72A.

*Flower size*.—About 4 mm in depth and 7 mm in diameter.

*Peduncles*.—Slightly oval in shape, primary; range from 5 to 10 cm in length, an average of 4 mm in width, secondary; average 1.3 cm in length and 1.5 mm in width, 183C in color, glabrous surface, peduncle leaves; an average of 2 per individual cyme, elliptic in shape, an average of 8 mm in length and 5 mm in width, N77A with slight tinge of N79C in color, glandular and slightly glaucous on upper and lower surfaces.

*Pedicels*.—Slightly oval in shape, an average of 2.5 cm in length and 1 mm in width, 183C in color, glabrous surface.

*Calyx*.—5-parted fused to tubular base, tips held nearly upright, about 2 cm in length and 2 cm in width.

*Sepals*.—5, tube; about 1.5 mm in length and 0.5 mm in width, 147A in color, tips about 2 mm in length and 1 cm in width, lanceolate in shape, 147A in color with small spots of 183C on both surfaces, entire margin, narrowly acute apex, fused base, glaucous on both surfaces.

*Petals*.—5, spreading, 3 mm in length and 1.5 mm in width, ovate-lanceolate in shape, truncate base, acute apex, entire margin, color of inner and outer surfaces when opening; a blend of NN155A and 64C, color of inner and outer surfaces when mature; becoming more heavily infused with 64C, translucent, glabrous on both surfaces.

Reproductive organs:

*Pistils*.—5, showy, held erect, about 3.5 mm in length, stigma; 1 mm in width and 155A in color, style; 2.5 mm in length, 1.5 mm in width, lanceolate in shape and color 64C with shading of 64A, ovary; small, single celled and translucent in color.

*Stamens*.—10, about 4 mm in length, filament; very fine and 155A in color and slightly suffused with 64B, anther; acorn-shaped, about 0.5 mm in length and width and 202A in color, pollen is moderate in quantity and about 13C in color.

*Fruit*.—Fruit and seed production has not been observed.

It is claimed:

1. A new and distinct variety of *Sedum* plant named 'Cherry Tart' as described and illustrated herein.

* * * * *